US012746147B2

(12) United States Patent
Patel

(10) Patent No.: US 12,746,147 B2
(45) Date of Patent: Sep. 29, 2026

(54) ANTI-SLEEP DISORDER ARTICLE

(71) Applicant: FINE COTTON FACTORY INC., Toronto (CA)

(72) Inventor: Biren Patel, Toronto (CA)

(73) Assignee: FINE COTTON FACTORY INC., Toronto (CA)

( * ) Notice: Subject to any disclaimer, the term of this patent is extended or adjusted under 35 U.S.C. 154(b) by 174 days.

(21) Appl. No.: 18/926,724

(22) Filed: Oct. 25, 2024

(65) Prior Publication Data

US 2025/0041104 A1 Feb. 6, 2025

Related U.S. Application Data

(63) Continuation-in-part of application No. 16/075,449, filed as application No. PCT/CA2017/050124 on Feb. 3, 2017, now abandoned.

(60) Provisional application No. 62/291,604, filed on Feb. 5, 2016.

(51) Int. Cl.

| | |
|---|---|
| ***A61P 25/20*** | (2006.01) |
| ***A61F 5/56*** | (2006.01) |
| ***A61K 9/00*** | (2006.01) |
| ***A61K 33/34*** | (2006.01) |
| ***B23B 5/02*** | (2006.01) |
| ***B32B 5/02*** | (2006.01) |
| ***B32B 5/26*** | (2006.01) |

(52) U.S. Cl.

CPC .............. *A61F 5/56* (2013.01); *A61K 9/0014* (2013.01); *A61K 33/34* (2013.01); *A61P 25/20* (2018.01); *B32B 5/02* (2013.01); *B32B 5/26* (2013.01); *B32B 2260/023* (2013.01); *B32B 2260/04* (2013.01); *B32B 2601/00* (2013.01)

(58) Field of Classification Search

CPC ......... A61F 5/56; A61P 25/20; A61K 9/0014; A61K 33/34; B32B 5/02; B32B 5/26

See application file for complete search history.

(56) References Cited

U.S. PATENT DOCUMENTS

| | | | | |
|---|---|---|---|---|
| 5,074,129 | A | 12/1991 | Matthew | |
| 5,299,335 | A | 4/1994 | Ivester et al. | |
| 5,806,525 | A | 9/1998 | Pope, Jr. | |
| 7,594,288 | B1 * | 9/2009 | Holliday | A47G 9/109 5/636 |
| 8,047,201 | B2 | 11/2011 | Guyuron et al. | |
| 9,403,041 | B2 | 8/2016 | Gabbay | |

(Continued)

FOREIGN PATENT DOCUMENTS

| | | |
|---|---|---|
| CA | 1334541 | 2/1995 |
| CA | 2900001 | 8/2014 |

(Continued)

OTHER PUBLICATIONS http://hzgongcheng.en.alibaba.com/product/60224817102-213384237wholesale_Copper_fibre_Antibacterial_Pillow_super_soft_and_comfortable.html.

(Continued)

*Primary Examiner* — Guy K Townsend

(57) ABSTRACT

A method of reducing or treating snoring, sleep apnea and other forms of sleep disordered breathing, comprising having a patient in need thereof sleep in contact with or in the proximity of an article containing copper. A fabric having anti-snoring, sleep apnea and other forms of sleep disordered breathing properties, the fabric comprising a copper.

12 Claims, 4 Drawing Sheets

(56) References Cited

U.S. PATENT DOCUMENTS

| | | | | |
|---|---|---|---|---|
| 9,469,923 | B2 | 10/2016 | Rudinger | |
| 2009/0173351 | A1* | 7/2009 | Sahin | A61F 2/02 128/848 |
| 2010/0226947 | A1* | 9/2010 | Theberge | A61K 8/0208 424/484 |
| 2011/0087115 | A1 | 4/2011 | Sackner et al. | |
| 2013/0115841 | A1* | 5/2013 | Ronner | D06C 15/02 28/165 |
| 2017/0087050 | A1 | 3/2017 | Lee | |
| 2019/0029870 | A1* | 1/2019 | Patel | A61K 33/34 |
| 2019/0374480 | A1* | 12/2019 | Patel | D06M 16/00 |
| 2020/0129546 | A1* | 4/2020 | Patel | A61P 27/02 |
| 2021/0205357 | A1* | 7/2021 | Patel | A61K 33/34 |
| 2023/0248764 | A1* | 8/2023 | Patel | A61K 9/7007 424/638 |
| 2025/0041104 | A1* | 2/2025 | Patel | A61K 33/34 |
| 2025/0276010 | A1* | 9/2025 | Patel | A61K 33/34 |

FOREIGN PATENT DOCUMENTS

| | | |
|---|---|---|
| WO | 2011096663 | 8/2011 |
| WO | 2012088507 | 6/2012 |
| WO | 2017136923 | 8/2017 |

OTHER PUBLICATIONS

"Fabric," Vocabulary.com Dictionary, https://www.vocabulary.com/dictionary/—(NFOA Jan. 1, 2021).

CuTEC, www.TextFiberTechnology.com; www.Nano-Glide.com; www.CuTEC29.com; Next Fiber Technology, LLC, 2014.

Office Action dated Feb. 27, 2024, issued in corresponding Canadian patent application No. 3,013,649.

International Preliminary Report on Patentability dated Feb. 3, 2017 issued in the corresponding International application No. PCT/CA2017/050124.

* cited by examiner

ANTI-SLEEP DISORDER ARTICLE

FIELD OF THE INVENTION

The present invention relates to articles containing copper useful for reducing or treating snoring, sleep apnea and other forms of sleep disordered breathing.

BACKGROUND OF THE INVENTION

A sleep disorder, or somnipathy, is a medical disorder of the sleep patterns of a person or animal. Some sleep disorders are serious enough to interfere with normal physical, mental, social and emotional functioning.

Sleep disorders are broadly classified into dyssomnias, parasomnias, circadian rhythm sleep disorders involving the timing of sleep, and other disorders including ones caused by medical or psychological conditions and sleeping sickness.

Some common sleep disorders include sleep apnea (stops in breathing during sleep), narcolepsy and hypersomnia (excessive sleepiness at inappropriate times), cataplexy (sudden and transient loss of muscle tone while awake), and sleeping sickness (disruption of sleep cycle due to infection). Other disorders include sleepwalking, night terrors and bed wetting.

Snoring is the vibration of respiratory structures and the resulting sound due to obstructed air movement during breathing while sleeping. In some cases, the sound may be soft, but in most cases, it can be loud and unpleasant. Snoring during sleep may be a sign, or first alarm, of obstructive sleep apnea (OSA). Snoring also may be produced by habit (common snoring).

Sleep apnea is generally defined as an intermittent cessation of airflow at the nose and mouth during sleep. Sleep apneas have been classified into three different types: central, obstructive and mixed. Central sleep apnea (CSA) is characterized by complete cessation of the activity of all respiratory muscles while OSA airflow is interrupted despite continuing respiratory neural drive. OSA occurs as a result of occlusion of the upper airway, usually at the level of the oropharynx, and is the most prevalent form of sleep apnea. Mixed apnea consists of an initial central component followed by obstructive apnea. In the following CSA will not be differentiated from OSA, and will be comprised by the term OSA.

The principal forms of treating or preventing OSA include surgery of the upper airway, intra-oral mandibular advancement devices and long-term treatment with positive airway pressure (PAP). PAP treatment operates by the generation of a mechanical airway splint counteracting airway collapse. Although technically effective this method is hampered by poor long-term compliance due to poor tolerance and frequent side effects from airway mucous membranes. Surgery and intra-oral mandibular advancement devices are not uniformly effective. In particular surgery has been associated with a considerable relapse of symptoms also in cases with initially excellent treatment results. Various forms of pharmacological treatment, e.g. acetazolamide, tricyclic antidepressants, theophylline, progesterone, and topiramate have been employed but have not gained wide clinical use.

Thus there is a need for an improved method for reducing, treating or preventing snoring, sleep apnea and other forms of sleep disordered breathing that does not involve surgical or pharmacological treatment of such disorders.

SUMMARY OF THE INVENTION

The present invention relates to articles with anti-snoring, anti-sleep apnea and other forms of sleep disorders, all of which are comprised by the term sleep disorder, properties. The present invention relates also to methods of reducing, preventing or treating a sleep disorder comprising the use of copper or articles containing copper by a person or subject or patient in need thereof.

In one embodiment the present invention is a method of treating a sleeping disorder, including snoring, sleep apnea and other forms of sleep disordered breathing, comprising having a patient in need thereof sleep in proximity to or in contact with an article containing copper.

In one embodiment of the method of treating a sleeping disorder, the sleep disorder is snoring or sleep apnea.

In another embodiment of the method of treating a sleeping disorder, the article containing copper is a fabric, a foam, a metallic object such as coins, copper wires, copper-containing metal sheets and so forth.

In another embodiment of the method of treating a sleeping disorder, the article is a fabric containing copper.

In another embodiment of the method of treating a sleeping disorder, the fabric containing copper includes a single layer.

In another embodiment of the method of treating a sleeping disorder, the fabric containing copper includes 2 or more layers, the two or more layers including a face layer and a back layer.

In another embodiment of the method of treating a sleeping disorder, the fabric containing copper includes 3 or more layers, the three or more layers including a face layer, an inlay and a back layer, and wherein the copper is contained in at least one of the inlay layer, the face layer and the back layer.

In another embodiment of the method of treating a sleeping disorder, the fabric containing copper is a ticking fabric for covering a mattress.

In another embodiment of the method of treating a sleeping disorder, the fabric containing copper is selected from a sheet, top of the bed product, mattress and mattress covers, removable mattress toppers, pillow cases, pillow shell, pillow fill, blanket and blanket fill, fitted and loose sheets for bedding, mattress pads, chair liners, clothing, towels or sleeping bag.

In another embodiment of the method of treating a sleeping disorder of the present invention, the copper in the article is in metallic form, salts or ionic form, wherein the metallic form includes particulates, alloys and oxides.

In another embodiment of the method of treating a sleeping disorder, the copper is copper oxide.

In another embodiment, the present invention provides for a method for reducing, preventing or treating a sleep disorder, including having a patient in need thereof sleep in proximity to or in contact with an article containing infused copper, where the article containing infused copper comprises between 0.05% to 4.5% copper by weight and is capable of releasing copper ions, and where the release of copper ions reduces, prevents or treats the sleep disorder.

In one embodiment, the present invention provides for a fabric having anti-sleep disorder properties including snoring, sleep apnea and other forms of sleep disordered breathing, the fabric comprising an effective amount of copper.

In one embodiment, the fabric comprises one or more layers, and wherein at least one of the one or more layers contains the copper.

In another embodiment, the fabric comprises a yarn containing copper.

In another embodiment, the sleep disorder is snoring or sleep apnea.

In another embodiment, the fabric includes 2 or more layers, and wherein the copper is contained in one or the two layers.

In another embodiment, the fabric includes 3 or more layers, the three or more layers including a face layer, an inlay and a back layer, and wherein the copper is contained in at least one of the inlay layer, the face layer and the back layer.

In another embodiment, the fabric is a ticking fabric for covering a mattress.

In another embodiment, the fabric includes one layer.

In another embodiment, the fabric is selected from a sheet, top of the bed product, mattress and mattress covers, removable mattress toppers, pillow cases, pillow shell, pillow fill, blanket and blanket fill, fitted and loose sheets for bedding, mattress pads, chair liners, clothing, towels or sleeping bag.

In another embodiment, the copper in the fabric is in metallic form, salts or ionic form, wherein the metallic form includes particulates, alloys and oxides.

In another embodiment, the present invention provides for a method for making a copper-containing fabric with anti-sleep disorder properties including snoring, sleep apnea and other forms of sleep disordered breathing, the method comprising:

(a) knitting a fabric on a circular weft knitting machine using a group of yarns consisting of various fibers or a combination thereof; and (b) introducing a thread or yarn containing copper (i) to the back of the fabric, (ii) to the face of the fabric, or (iii) as a filler between the face and the back of the fabric, or in any combination of (i), (ii) and (iii) thereof.

In another embodiment, the present invention relates to a use of an article containing copper for reducing, preventing or treating a sleep disorder.

In one embodiment of the use, the sleep disorder is snoring or sleep apnea.

In another embodiment of the use, the article containing copper is a fabric, a foam, a metallic object such as coins, copper wires, copper-containing metal sheets and so forth.

In one embodiment of the use, the article is a fabric containing copper.

In one embodiment of the use, the fabric has one or more layers, and wherein at least one of the one or more layers contains copper.

In one embodiment of the use, the fabric comprises a yarn containing copper.

In one embodiment of the use, the fabric comprises 2 or more layers, and wherein the copper is contained in at least one of the two or more layers.

In one embodiment of the use, the fabric comprises 3 or more layers, the three or more layers including a face layer, an inlay and a back layer, and wherein the copper is contained in at least one of the inlay layer, the face layer and the back layer.

In one embodiment of the use, the fabric is a ticking fabric for covering a mattress.

In one embodiment of the use, fabric has one layer.

In one embodiment of the use, the fabric is selected from a sheet, top of the bed product, mattress and mattress covers, removable mattress toppers, pillow cases, pillow shell, pillow fill, blanket and blanket fill, fitted and loose sheets for bedding, mattress pads, chair liners, clothing, towels or sleeping bag.

In one embodiment of the use, the copper in the article is in metallic form, salts or ionic form, wherein the metallic form includes particulates, alloys and oxides.

In another embodiment according to any of the previous embodiments of the present invention, the content of copper in the articles by weight is between about 0.05% to 4.5%.

BRIEF DESCRIPTION OF THE DRAWINGS

The following figures illustrate various aspects and preferred and alternative embodiments of the invention.

FIG. 5: capture of a snoring management app.

DESCRIPTION OF THE INVENTION

Definitions

Figure 1:
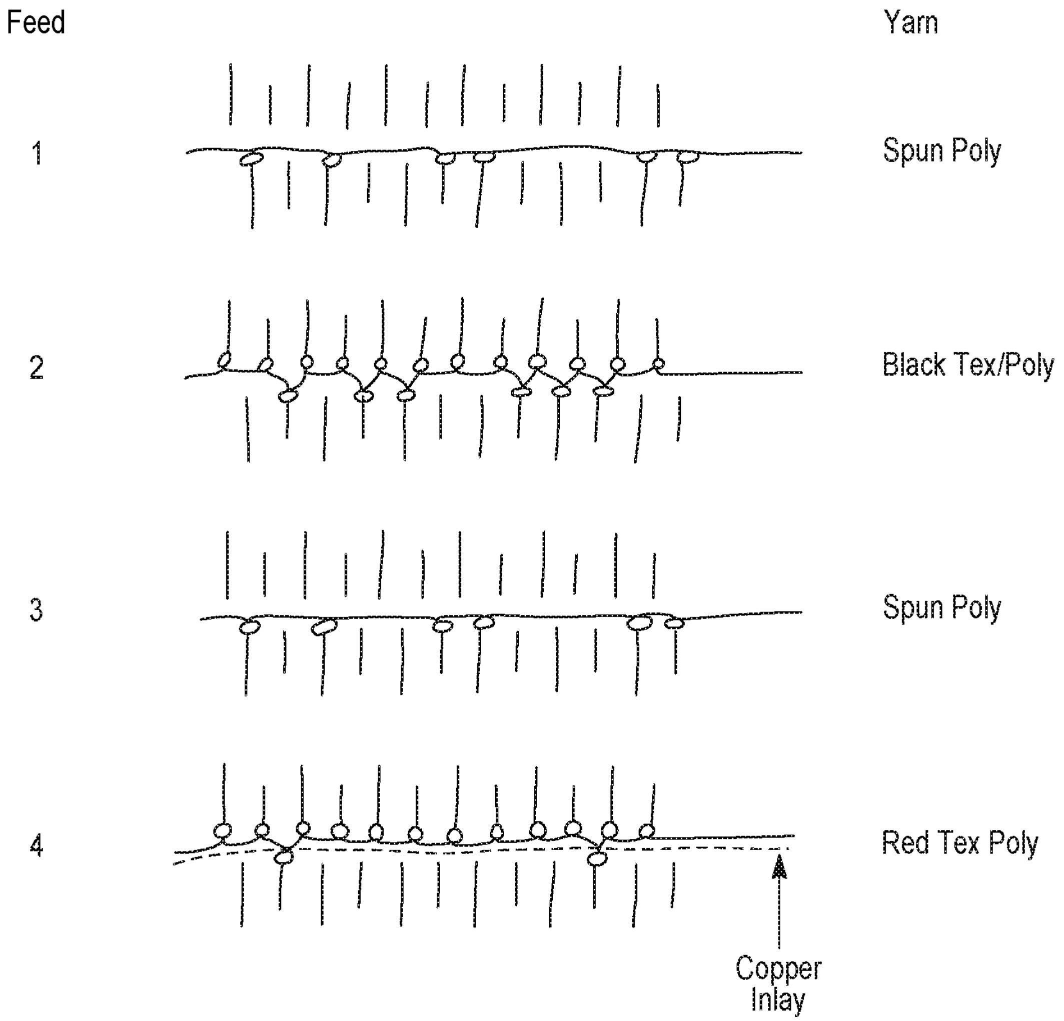
FIG. 1: illustration of a knitting sequence of a copper-containing fabric according to one embodiment of the present invention.

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise. In order to aid in the understanding and preparation of the within invention, the following illustrative, non-limiting, examples are provided.

The term "knit" may be used as a verb (to make (a fabric or garment) by interweaving yarn or thread in a series of connected loops either by hand, with knitting needles, or on a machine) or as a noun (a fabric or garment made by knitting).

"Fiber" and "fibers" refer to any slender, elongated structure that can be carded or otherwise formed into a thread. Examples of fibers include "stable fibers," a term that is well-known in the textile art.

"Yarn" refers to a structure comprising a plurality of threads.

"Effective amount" as used herein is meant an amount of copper content in an article, high enough to significantly positively modify the condition to be treated but low enough to avoid serious side effects (at a reasonable benefit/risk ratio), within the scope of sound medical judgment.

The present invention discloses the use of copper in reducing or treating sleep related conditions or disorders, such as for reducing and controlling snoring and sleep apnea. In one embodiment of the present invention the copper may be provided in textiles or fabrics with anti-Obstructive Sleep Apnea (OSA) properties, including snoring and sleep apnea. The applicant has shown that copper contained in articles such as textiles, foams and fabrics reduce snoring. The textiles or fabrics may be manufactured with copper-containing yarns, or may be infused, embedded or impregnated with copper. Foams may be infused, embedded or impregnated with copper. The copper—may be in metallic form (e.g., particulates, alloys and oxides), salts and/or ionic form. In some embodiments, an article containing infused copper, such as a fabric in accordance with the present disclosure (e.g., an article containing infused copper of between 0.05% to 4.5% copper by weight) may be infused with a solution containing 1.0-2.0 micron particles of copper.

In some embodiments, an article containing infused copper, such as a fabric in accordance with the present disclosure (e.g., an article containing infused copper of between 0.05% to 4.5% copper by weight) is capable of releasing copper ions. In some embodiments, a fabric in accordance with the present disclosure (e.g., a fabric containing infused copper of between 0.05% to 4.5% copper by weight) is capable of releasing copper ions. In some embodiments, the release of copper ions can reduce, prevent or treat a sleep disorder.

In another embodiment, the copper may be provided on its own. For example, a subject may sleep in the proximity of or in contact with copper or copper containing objects or articles, such as copper coins, cables with copper wires, naked copper wires, and so forth. By “in the proximity” is meant that the subject is not in direct contact with the copper, but effectively close to the copper to positively exert its anti-sleep disorder properties. The proximity may vary with the duration of the exposure, the nature of any barriers between the copper-containing article and the subject, the number of barriers between the copper-containing article and the subject, the distance between the copper and the subject or any combination thereof. For example, the copper may be restricted to the inlay of a three-layer fabric, as such there would be at least one layer of fabric between the copper and the subject. Subject to the nature of the barrier, the effective proximity to exert anti-sleep disorder properties will thus be the maximum distance between the copper in the article and the subject, or the maximum number of barriers between the copper and the subject which will provide the desired effect on the subject’s sleep disorder.

The textile or fabric of the present invention may be made using a yarn comprising a polymer or cellulose, or regenerated cellulose, or otherwise, and copper. The copper may be provided as a powder, liquid or alloy forms. Polymers include a compound suitable for fiber and fabric generation including a thermoplastic polymer, polyester, nylon, rayon, polyethylene (PE), polypropylene (PP), polyethylene terephthalate (PET), polyethylene terephthalate glycol (PETG), co-PET, polylactic acid (PLA), and polytrimethylene terephthalate (PTT).

In some embodiment, the yarn of the present invention may be copper-containing fiber. An example of a copper-containing fiber is described in WO/2012/088507, the content of which is incorporated herein by reference.

In another embodiment, the textiles or fabrics of the present invention may contain copper attached, coupled or connected to the fabric, or the copper may be loose. For example, the fabric may be in the form of a bag having copper inside the bag in loose form or attached to the inside walls of the bag, or copper may be attached, connected, or coupled to an existing fabric. Alternatively, the fabric may contain one or more pockets into which the copper can be contained in loose or attached form. The pockets may be designed to be in a closed or opened from. For example, the pocket may include attachment means such as buttons or Velcro® or may include a flap to open or close the pocket. This design of pockets may allow a person to insert or remove the copper from the pockets. Copper may be provided in any form as previously described. For example, the copper may be provided as a powder, liquid, alloys, filaments, wires, or in the form of coins (for example one cent coins known as pennies). The copper may be provided in metallic form, salt from or ionic form.

The fabric of the present invention may have one, two, three, four or more than four layers. A three layer fabric (with inlay), ticking fabric and/or double knit fabric (two layer without inlay), and/or a single knit construction of any kind, or a woven of any kind or content. The copper may be included any one of the layers of the fabric, and in more than one layer. For example, in a two layer fabric, the copper may be included in both layers, or in just one layer. In a three layer fabric having a top, middle and bottom layers, the copper may be included in just one of the 3 layers (in any of the top, middle or bottom layers), in 2 of the 3 layers (in any combination of two of the top, middle or bottom layers) or in all of the 3 layers.

The applicant surprisingly discovered that the benefits of copper to reduce/treat a sleep disorder, such as snoring, can be achieved even when the copper is contained in the inlay of a fabric in accordance with the present disclosure, such as a fabric containing infused copper of between 0.05% to 4.5% copper by weight, i.e. where the fabric containing infused copper was not in direct contact with the subject using the fabric. A fabric in accordance with the present disclosure, such as a fabric containing infused copper of between 0.05% to 4.5% copper by weight, is capable of releasing copper ions. By contrast, tests on other known fabrics having the copper (e.g., other known copper-infused fabrics) only in the inlay have been shown to not release copper ions. Furthermore, a fabric in accordance with the present disclosure, such as a fabric containing 30% of copper-infused yarn, for example containing between 0.05% to 4.5% copper by weight, as described herein, demonstrated an ohm meter reading of 3 to the power of ten. By contrast, ohm meter tests of other known copper-infused fabrics did not result in measurable ohm meter readings.

As such, the results of obtained in Example 1 below, in which the copper was restricted to the inlay (i.e. not in contact with the study participant) are surprising.

In the case of a three layer fabric, yarn position on the three layer fabric may be as follows:

1) All face feeds: copper-containing fiber; all inlay feeds: polymer filaments; and/or all back feeds: polymer filaments.
2) All face feeds: polymer fiber; all inlay feeds: copper-containing fiber; and/or all back feeds: polymer filaments.
3) All face feeds: polymer filaments; all inlay feeds: polymer filaments; and/or all back feeds: copper-containing fiber.

The yarn can be used by itself or with any other known and unknown fibers. Known fibers, such as Celliant, coolmax, cellulose fibers, FR. Fibers, infrared yarn, natural or manmade fiber, either as outer layer or inner layer as long as content of Cu content by weight is between about 0.05% to 4.5% by weight. Total content of this yarn in the fabric or textile of the present invention may be anywhere between about 8.5% to about 91.2% of the total in the fabric, including 9%, 10%, 15%, 20%, 25%, 30%, 35%, 40%, 45%, 50%, 55%, 60%, 65%, 70%, 75%, 80%, 85%, 90%, 100% and any percentage there in between. In some embodiments, an article containing infused copper may be a fabric including 30% copper infused yarn. In some embodiments, an article containing infused copper may be a fabric including 10% copper infused yarn.

This yarn may be spun or filament and may be used on one layer or in multiple layer fabrics. The fabric can be made using known technologies, such as knitting technology, woven technology or non-woven technology.

The fabric may be made using elastane yarn (i.e. Spendex® or Lycra®).

The copper-containing fabric or textile of the present invention having anti-sleep disorder properties including snoring, sleep apnea and other forms of sleep disordered breathing may be manufactured by any method known in the art. In one embodiment, the process for making the copper-containing fabric properties includes:

(a) knitting a fabric on a circular weft knitting machine (or dial selection machine, or any other such type of knitting or weaving machine as may be invented during the term of this patent) using a group of yarns consisting of various fibers or a combination thereof;
(b) introducing a copper thread or yarn to the back of the fabric, referring to the dial in any combination of other fibers; or
(c) introducing a copper thread or yarn to the face of the fabric, referring to the cylinder in any combination of other fibers; or
(d) introducing a copper thread as a filler, referring to the space between the face and the back of the fabric in any combination of other fibers.

The knitting machine may be of various diameters and gauges and a combination thereof. The thread or yarns may be of various colors, counts or deniers and any combination thereof.

The process of manufacture may also include the use of various knitted structures and a combination thereof. Full and half gauge structures are also included and a combination thereof.

Figure 2:
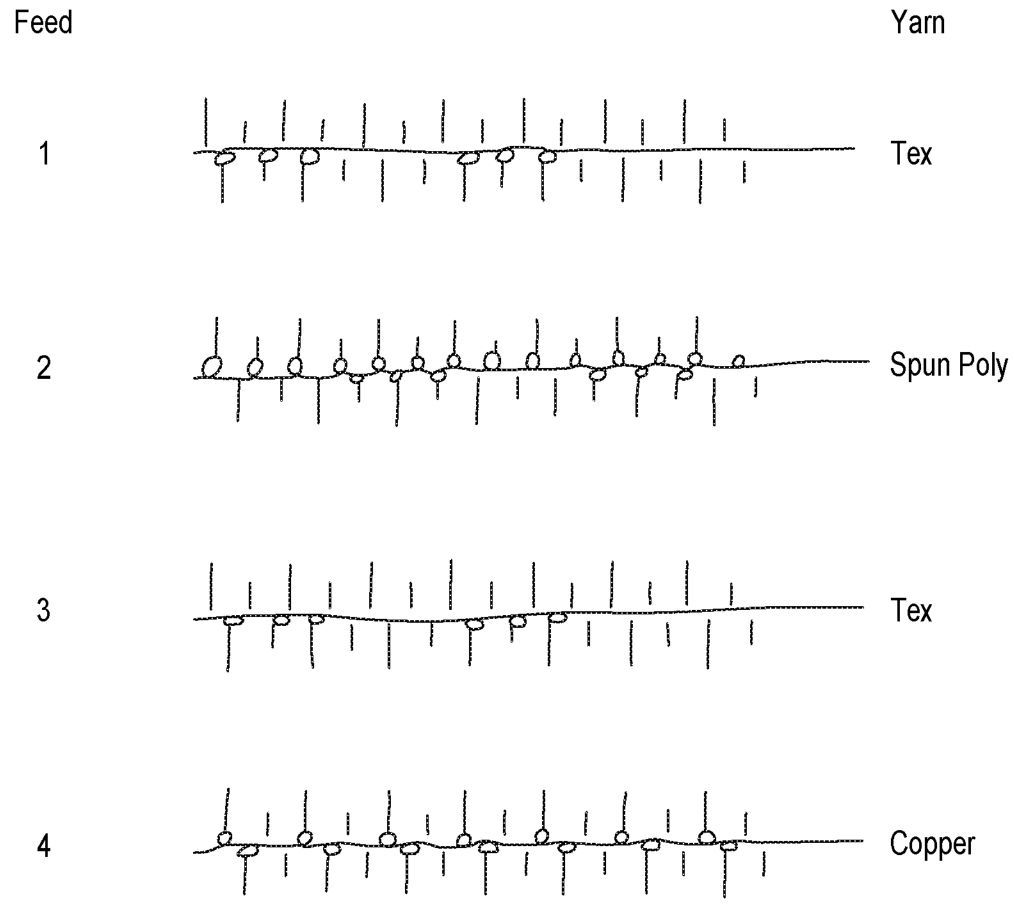
FIG. 2: illustration of a knitting sequence of a copper-containing fabric according to another embodiment of the present invention.
Figure 3:
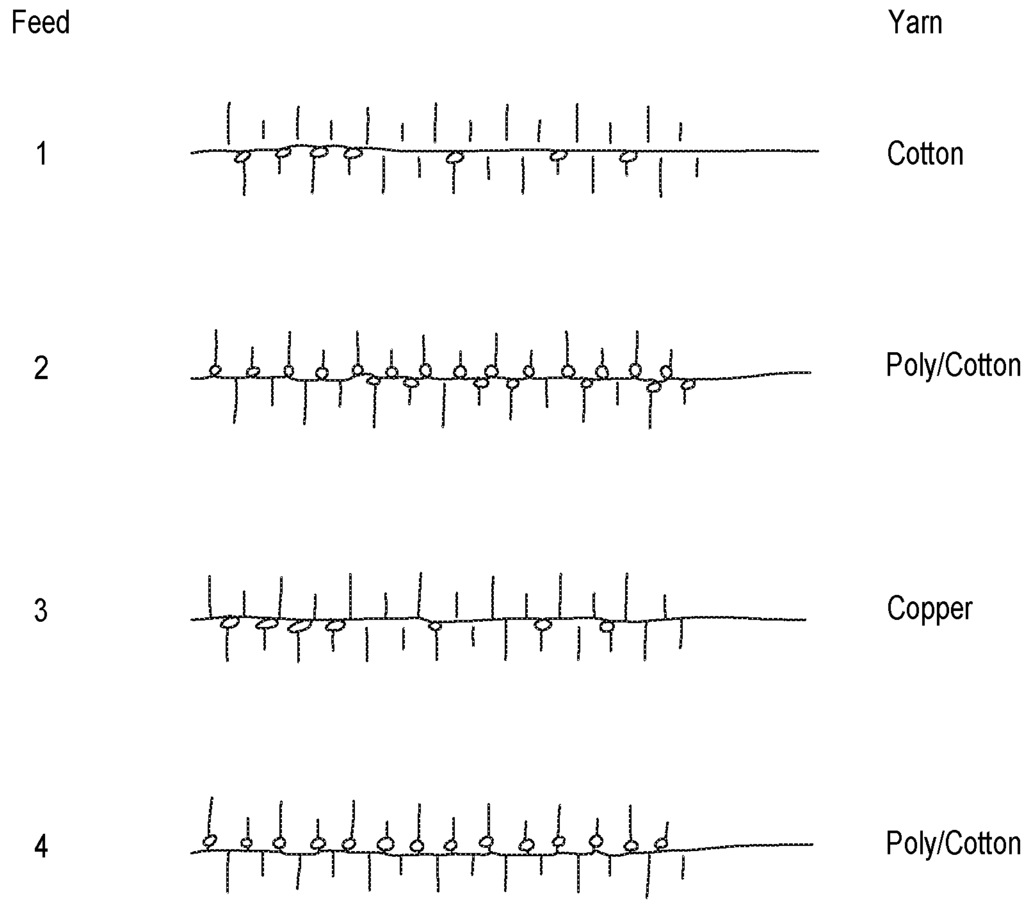
FIG. 3: illustration of a knitting sequence of a copper-containing fabric according to another embodiment of the present invention.
Figure 4:
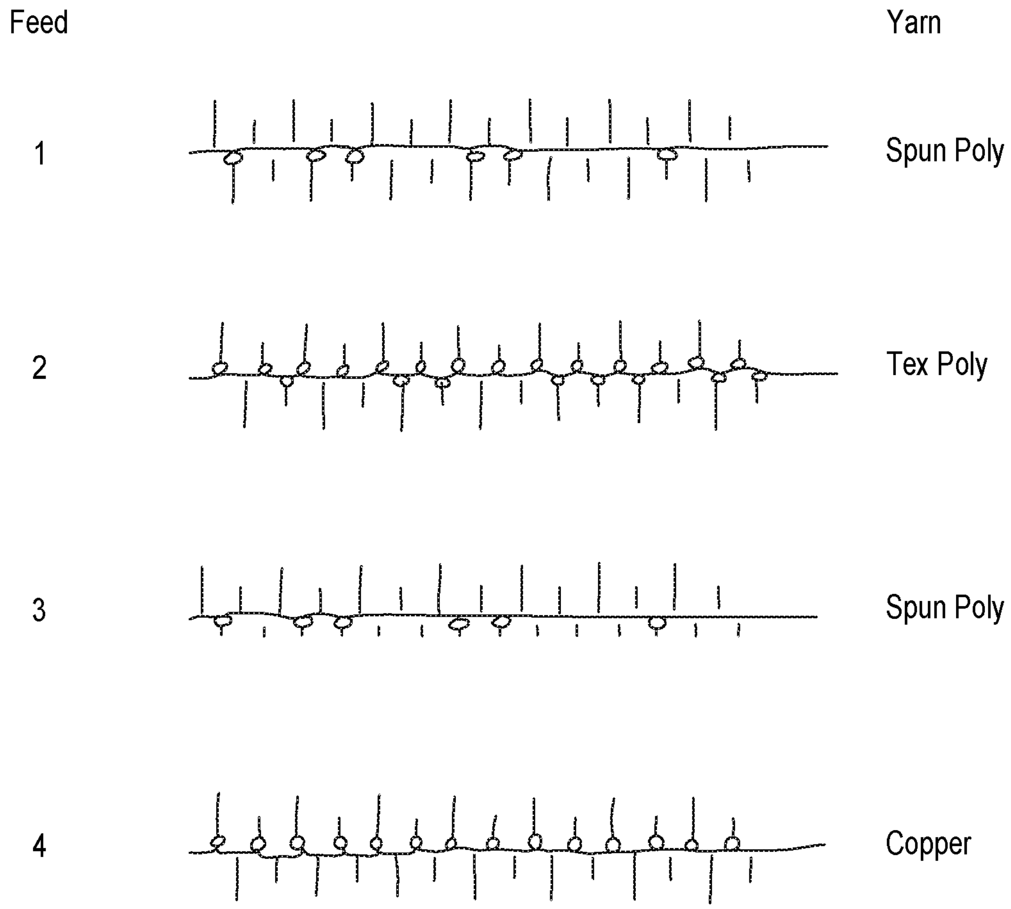
FIG. 4: illustration of a knitting sequence of a copper-containing fabric according to another embodiment of the present invention.

FIGS. 1-4 illustrate non-limiting knitting sequences of a copper-containing fabric according to different embodiments of the present invention.

Tables 1-4 illustrate the knitting sequences for FIGS. 1-4 respectively.

TABLE 1

| Feed # | Dial set out | Cylinder set out | Yarn |
|---|---|---|---|
| 1 | Welt all | Select as per design | Spun poly |
| 2 | Knit all | Select as per design | Black tex/Poly |
| 3 | Welt all | Select as per design | Spun Poly |
| 4 | Welt all | Select as per design | Red Tex/Poly + copper inlay* |

*does not knit, the copper is sandwiched between face and back of fabric

TABLE 2

| Feed # | Dial set out | Cylinder set out | Yarn |
|---|---|---|---|
| 1 | Welt all | Select as per design | Tex poly |
| 2 | Knit all | Select as per design | Spun Poly |
| 3 | Welt all | Select as per design | Tex Poly |
| 4 | Knit all | Select as per design | Copper** |

**Copper is knitting on dial and cylinder feed and showing on both face and back of fabric.

TABLE 3

| Feed # | Dial set out | Cylinder set out | Yarn |
|---|---|---|---|
| 1 | Welt all | Select as per design | Cotton |
| 2 | Knit all | Select as per design | Poly/cotton |
| 3 | Welt all | Select as per design | Copper*** |
| 4 | Knit all | Select as per design | Poly/cotton |

***Copper is knitting on cylinder only feed and showing on face only.

TABLE 4

| Feed # | Dial set out | Cylinder set out | Yarn |
|---|---|---|---|
| 1 | Welt all | Select as per design | Spun poly |
| 2 | Knit all | Select as per design | Tex/Poly |
| 3 | Welt all | Select as per design | Spun Poly |
| 4 | Knit all | Select as per design | Copper**** |

****Copper is knitting on dial only feed and showing on back only.

Alternatively, the fabric containing copper of the present invention may include a woven or non-woven textile that has been impregnated in or coated with copper. Jeffrey Gabbay et al. (J. of Industrial Textiles, vol. 35, issue 4, 2006, p. 323, the contents of which are incorporated herein by reference) provide an example on impregnating textiles with copper oxide. "Briefly, cotton fibers are plated as follows: cationic copper (a mix of $Cu^{2+}$ and $Cu^{1+}$) is bound to cellulose-based fibers. Cotton, rayon/viscose, and fibers such as lyocel by Tencel are treated with an electroless plating process, which includes the following steps: (a) fibers having a diameter of about 11-13 mm are soaked for 5 s in 1% SnCl2, pH 3.5 at room temperature; (b) the fibers are then soaked for 5 s in PdCl2, pH 4 at room temperature, producing activated fibers; and (c) the activated cellulose based fibers are then exposed to formaldehyde, $CuSO_4$, and polyethylene glycol at pH 9. After about 5 min the fibers are plated with cationic copper (Cu(II) and Cu(I)). Finally, the fibers are dried and run through a textile carding machine which separates and aligns them.

"Impregnation of copper into the various synthetic fibers mentioned above is achieved by adding a cupric oxide powder to the polymers during the master batch preparation stage. The master batch can be made in industrially accepted concentrations and added to the polymeric slurry the same way any other master batch would be added, such as for pigmentation, etc. The copper oxide doped master batch is designed in such a way as to allow fiber extrusion in the normal production systems. The fibers can be cut into short staple or produced in filament form and texturized, if so desired. As in the case of the plated fibers mentioned above, the product yielded is a fiber that can be introduced at the blending stage of yarn production or directly into a woven or knit product so that no manufacturing processes are changed." (See Jefferey Gabbay et al (supra) at p. 325).

The articles of the present invention, including foam, fabric or textile may have different applications, including (i) top of the bed product, (ii) mattress and mattress covers, (iii) removable mattress toppers, (iv) pillow cases, (v) pillow shell, (vi) pillow fill, (vii) blanket and blanket fill, (viii) fitted and loose sheets for bedding, (xi) mattress pads, (xii) chair liners, (xiii) sleeping bags, (xiv) clothing, including pajamas, socks and so forth, (xv) towels, (xvi) in hospital settings in mattress/toppers/removable covers/all related to mattress or any resting or sleeping surface, and (xvii) in mattresses.

In order to aid in the understanding and preparation of the within invention, the following illustrative, non-limiting, examples are provided.

EXAMPLE 1

Materials and Methods

In-house study was conducted during the period of Oct. 12, 2015 to Dec. 15, 2015. Participant inclusion/exclusion criteria included:

1. Must be couple
2. Must be sleeping in same room with partner
3. One or both partner must snore during night A fabric of the present invention (a 3 layer ticking fabric) was provided to each couple and instructed to place this fabric on the bed and were instructed to sleep on it so that the body can continuously contact with the sleeper to observe changes and benefits to their sleeping patterns and observe level of snoring. We had given this fabric to 6 couples and were required to fill survey sheet in the morning after each night of sleeping on the fabric preferably approximately same time in each morning. This experiment was carried out for 7 consecutive nights.

Results

After One Night:

1. After a one night sleep on the product, four couples reported considerable reduction in snoring.
2. Two couples reported no change
3. All couples reported better night sleep.
4. One couple reported waking up during the night
5. Three couples reported less pain in joints and feeling refresh.

After Seven Nights:

1. Two couples reported no snoring, four couples reported that their partner did snore but the noise was substantially lower and they were not disturbed with the noise (i.e. reduced snoring).
2. Two couples who had high blood pressure and are on medicine reported a reduction in their blood pressure than normal.
3. All six couples reported their skin and texture were noticeably improved.
4. Four couples reported reduction in dark circle under the eyes.
5. Three couples reported less or no pain in joints.
6. One sleep apnea patient reported significant improvement and thinks that he may not have it any more. Due to sleep apnea and anxiety condition, he was not able to drive on Highways. Now he has no problem driving on highways.

FIG. 5 illustrates the sleeping pattern of one participant for a total of 4 days taken during the month of January 2017, corroborating the results of the present study. The first day is without the fabric containing copper, while the following days is with copper-containing fabric. A reduction of 20-25% in snoring can be seen in FIG. 5. The app used is the SnoreClock by Ralph's Apps, Weltzienstr. 2 76135 Karlsruhe Germany.

Feedback from Study Participant

The following feedback from a study participant was collected:

"Having played hockey most of my life, and being almost 60 and an active golfer, I struggled with back, knee and ankle stiffness, pain, and discomfort in general. In early December 2015, I was given by the Applicant 2 yards of fabric to sleep on. On the morning after I had slept on it for the first time, I did feel better first thing in the morning, no doubt about it.

"Later in the day, my wife said I hadn't snored the previous night. My snoring was at a level that concerned my family, so they easily noticed that I went through a night without snoring. When my wife mentioned that, I never connected the dots. Until it happened the second night in a row.

"When she told me the next day, early in the morning I hadn't snored again.

The following night I slept in the spare bedroom on a regular bed, and my snoring was restored to its usual level. The following night I slept on the provided fabric again, and my snoring was reduced to a minimal level.

"I sleep on copper containing fabrics every night since. When I travel with my wife, she says the snoring returns the night I'm off the fabric, and ceases when I get back home and get back on my copper fabric."

EXAMPLE 2

Studies were carried out as in Example 1 with fabrics that are manufactured using the copper containing yarn in various layers and positions; using the copper-containing yarn in conjunction with other health beneficial yarns, such as infrared, Celliant, Milk, natural and man-made; and different content of copper in the fabric.

Through the embodiments that are illustrated and described, the currently contemplated best mode of making and using the invention is described. Without further elaboration, it is believed that one of ordinary skill in the art can, based on the description presented herein, utilize the present invention to the full extent. All publications cited are incorporated by reference.

What is claimed is:

1. A method of reducing, preventing or treating a sleep disorder, comprising having a patient in need thereof sleep in proximity to or in contact with an article containing infused copper, wherein the article containing infused copper comprises between 0.05% to 4.5% copper by weight and is capable of releasing copper ions, and wherein the release of copper ions reduces, prevents or treats the sleep disorder.

2. The method of claim 1, wherein the sleep disorder is snoring or sleep apnea.

3. The method of claim 1, wherein the article containing infused copper is a fabric or a foam.

4. The method of claim 1, wherein the article is a fabric containing infused copper.

5. The method of claim 4, wherein the fabric containing infused copper includes a single layer.

6. The method of claim 4, wherein the fabric containing infused copper includes 2 or more layers, and wherein the infused copper is contained in at least one of the two or more layers.

7. The method of claim 4, wherein the fabric containing infused copper includes 3 or more layers, the three or more layers including a face layer, an inlay and a back layer, and wherein the infused copper is contained in at least one of the face layer, the inlay layer and the back layer.

8. The method of claim 4, wherein the fabric containing infused copper is a ticking fabric for covering a mattress.

9. The method of claim 4, wherein the fabric containing infused copper is selected from a sheet, top of the bed product, mattress and mattress covers, removable mattress toppers, pillow cases, pillow shell, pillow fill, blanket and blanket fill, fitted and loose sheets for bedding, mattress pads, chair liners, clothing, towels or sleeping bag.

10. The method of claim 4, wherein the fabric containing infused copper comprises 30% copper-infused yarn.

11. The method of claim 4, wherein the fabric containing infused copper comprises 10% copper-infused yarn.

12. The method of claim 1, wherein the infused copper is in metallic form, salts or ionic form, wherein the metallic form includes particulates, alloys and oxides.

* * * * *